(12) United States Patent
Lee

(10) Patent No.: US 6,537,292 B1
(45) Date of Patent: *Mar. 25, 2003

(54) LANCET HAVING A BLOOD-COLLECTING NEEDLE WITH A SAFETY FEATURE

(75) Inventor: Choon-Bal Lee, Gicheung-101, Dongheung Villa, 787-4, Kyesan-dong, Kyeyang-ku, Incheon-shi (KR)

(73) Assignees: Choon-Bal Lee, Incheon-shi (KR); Baek-Shik Shin, Incheon-shi (KR)

( * ) Notice: Subject to any disclaimer, the term of this patent is extended or adjusted under 35 U.S.C. 154(b) by 186 days.

This patent is subject to a terminal disclaimer.

(21) Appl. No.: 09/669,453

(22) Filed: Sep. 25, 2000

(30) Foreign Application Priority Data

May 25, 2000 (KR) .............................. 00-14890

(51) Int. Cl.[7] .............................. A61B 17/32
(52) U.S. Cl. ....................... 606/182; 606/181
(58) Field of Search ................. 606/181, 182, 606/183, 184, 185; 600/573, 576, 578, 538

(56) References Cited

U.S. PATENT DOCUMENTS

| | | | | |
|---|---|---|---|---|
| 4,653,513 A | * | 3/1987 | Dombrowski | 600/578 |
| 5,314,442 A | * | 5/1994 | Morita | 606/182 |
| 5,318,584 A | * | 6/1994 | Lange et al. | 606/167 |
| 5,666,966 A | * | 9/1997 | Horie et al. | 600/573 |
| 5,857,983 A | * | 1/1999 | Douglas et al. | 600/573 |
| 5,873,887 A | * | 2/1999 | King et al. | 600/583 |
| 6,210,420 B1 | * | 4/2001 | Mauze et al. | 606/181 |

* cited by examiner

*Primary Examiner*—Danny Worrell
(74) *Attorney, Agent, or Firm*—Lowe Hauptman Gilman & Berner, LLP

(57) ABSTRACT

A lancet having a blood-collecting needle with a safety feature, can prevent blood-mediated infections of AIDS, hepatitis, or other pathogenic bacteria due to careless impalement of a person collecting blood or handling waste disposition thereafter, by disposing a cap with a blood-collecting needle and repositioning the point end of the needle inside the cap via a return spring after collecting blood.

1 Claim, 6 Drawing Sheets

ABSTRACT-FREE BODY

LANCET HAVING A BLOOD-COLLECTING NEEDLE WITH A SAFETY FEATURE

FIELD OF THE INVENTION

The present invention relates to a lancet having a blood-collecting needle with a safety feature. In particular, the present invention relates to a lancet having a blood-collecting needle with a safety feature, which can prevent blood-mediated infections of AIDS, hepatitis, or other pathogenic bacteria due to careless impalement of a person collecting blood or handling waste disposition thereafter. This is accomplished by means of disposing a cap with a blood-collecting needle by repositioning the point end of the needle inside the cap via a return spring after collecting blood therein.

BACKGROUND OF THE INVENTION

A conventional lancet has a needle 9, as illustrated in FIG. 1, inserted into the center of a body 6, the frontal part 9 of which is connected to a detachment cap 7 which temporarily protects the terminal part of the needle 9. In using a blood-collecting needle 5, the detachment cap 7 is separated therefrom to expose the needle 9. While collecting blood, the needle 9 is set up inside the cap 3 of a cylinder 1 which is used as a gun (as shown in FIG. 2). However, in separating the blood-collecting needle 5 from the gun after collecting blood, the needle 9 becomes exposed, which may pose a risk to a person collecting blood, who can be infected with AIDS, hepatitis or other pathogenic bacteria by means of an accidental prick of the needle 9. Moreover, the blood-collecting needle 5 is not only small in size, but also the exposure thereof after use cannot be easily identified by the naked eye. Consequently, a person handling waste disposition after blood collection is also at risk of becoming infected with AIDS, hepatitis or other pathogenic bacteria by an accidental prick of the needle 9. In the Figures, those parts not explained in detail, or the parts 2, 4 and 8 as illustrated are a button, a clip, and a detachment part, respectively.

SUMMARY OF THE INVENTION

The present invention was designed to solve the aforementioned problems, with the objective of providing a lancet having a blood-collecting needle with a safety feature. In particular, the present invention relates to a lancet having a blood-collecting needle with a safety feature, which can prevent blood-mediated infections of AIDS, hepatitis, or other pathogenic bacteria due to careless impalement of persons collecting blood or handling waste disposition thereafter, by means of disposing a cap with the blood-collecting needle by repositioning the point end of the needle inside the cap via a return spring.

In order to achieve the aforementioned objectives, the present invention provides a lancet having a safety feature on a blood-collecting needle, which comprises as follows: a cap of a barrel body, having its lower part narrower than the upper part, assembled as such with two sections; a screw thread corresponding to said cap connecting screw on the inner circumference of the upper part of the cap; a stop projection protruding from the lower part thereof; a stroke stop projection at the inner surface of the lower part of the cap, from a certain distance from said stop projection; a needle stop projection at the slot; a plate-like elastic return spring at the inside base of the cap; a stop ring at the upper part of the body in which a needle is installed; a connecting rod at the upper part of the blood-collecting needle, attach- ing or detaching from the connecting encasement; a square fixed ring at the lower part thereof; a body fixed screw, at the lower part thereof, corresponding to said needle stop projection; and a detachment knob at the lower part of the blood-collecting needle.

BRIEF DESCRIPTIONS OF THE DRAWINGS

DESCRIPTION OF THE PREFERRED EMBODIMENT

Figure 1:
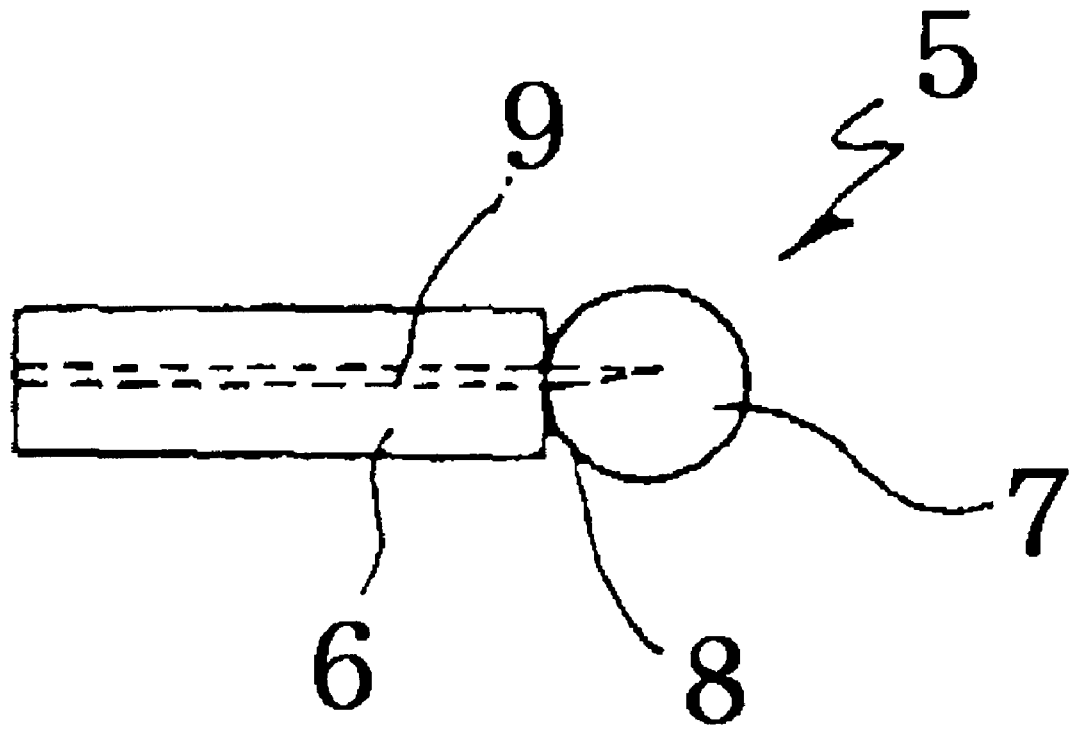
FIG. 1 is a plane view of a conventional blood-collecting needle.
Figure 2:
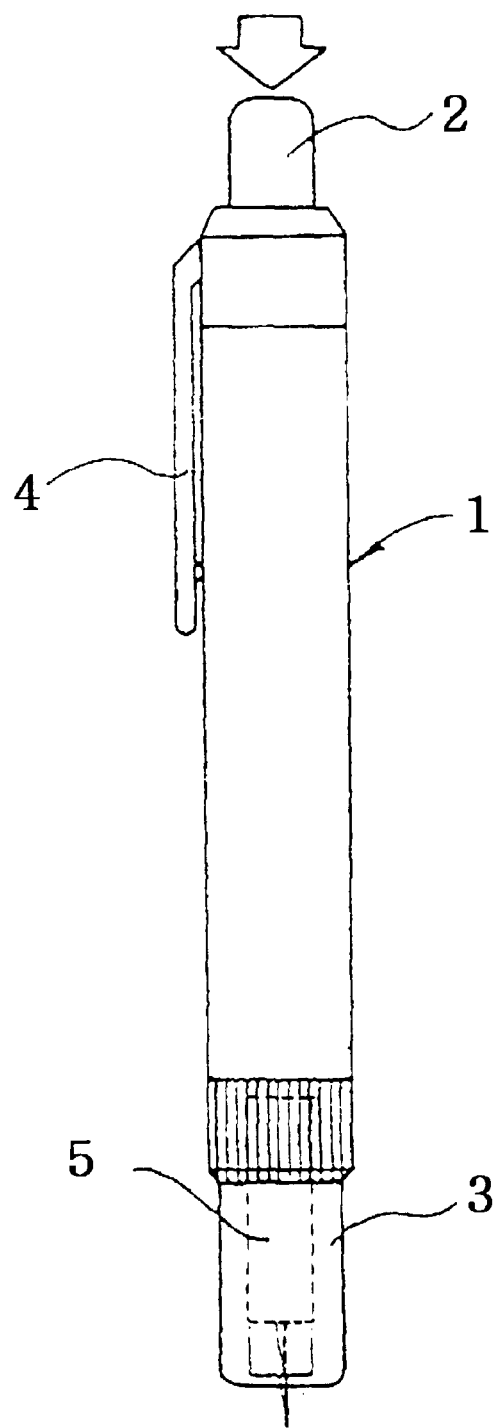
FIG. 2 is a lateral view of a conventional blood-collecting cylinder.
Figure 3:
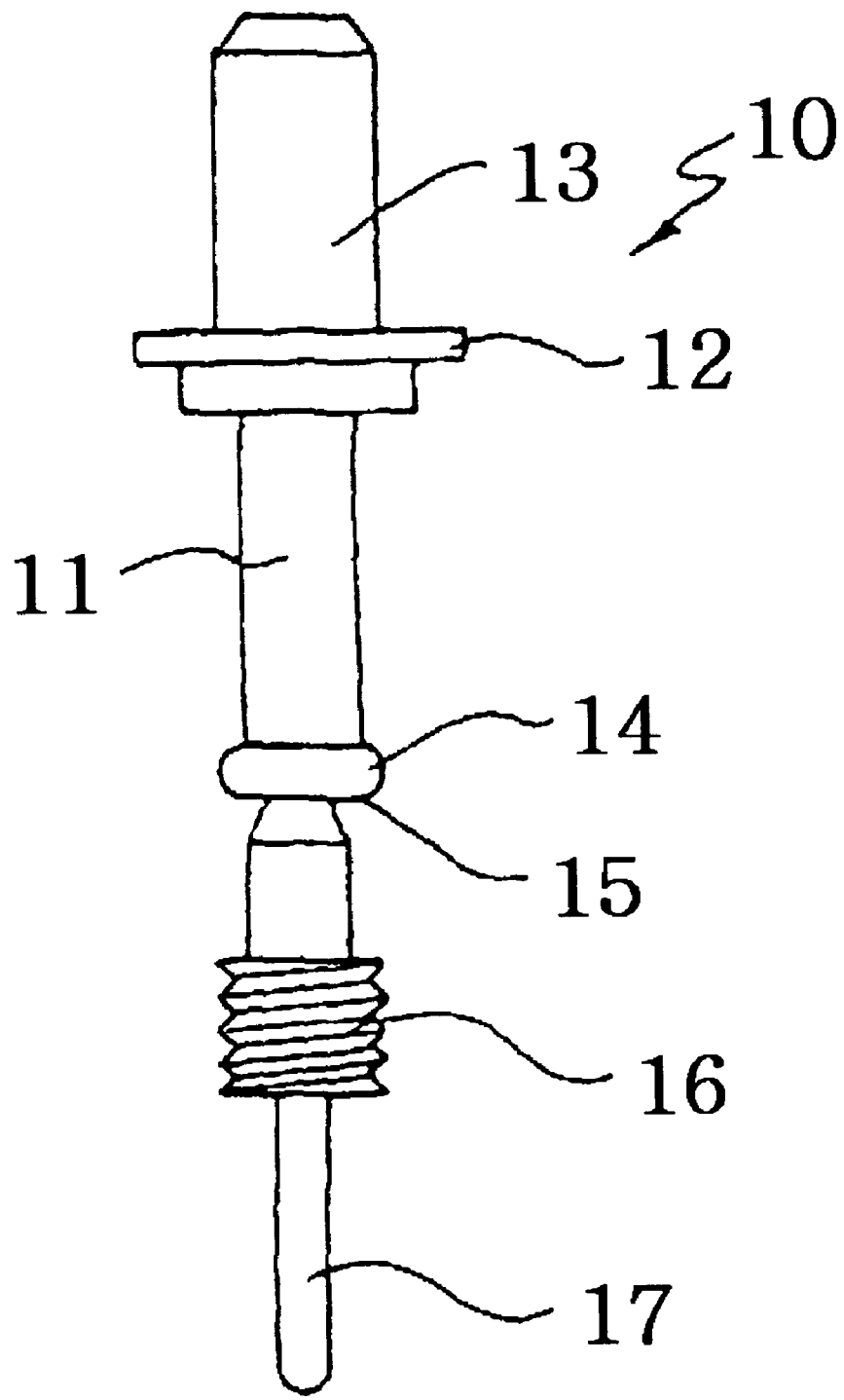
FIG. 3 is a lateral view of the blood-collecting needle according to the present invention.
Figure 4:
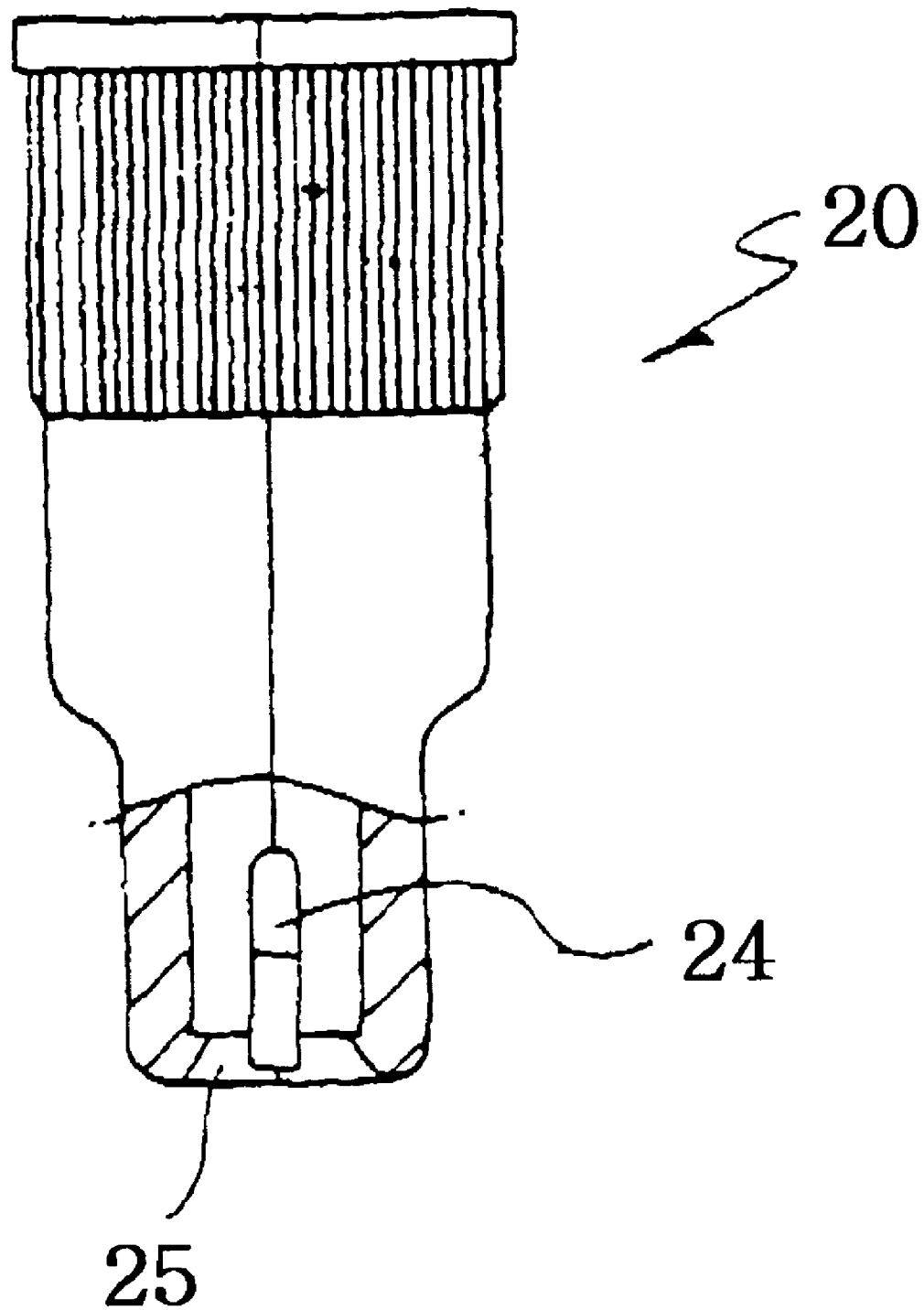
FIG. 4 is a lateral view of the cap according to the present invention.

The present invention is described in detail with references to the attached Figures. In FIGS. 3 and 4, a lancet having a blood-collecting needle with a safety feature according to the present invention is illustrated, which comprises a blood-collecting needle 10 and a cap 20.

The blood-collecting needle 10 comprises a needle 18 installed vertically inside a body 11; a disk-like stop ring 12 in the upper part of said body; a connecting rod 13 at the upper part thereof seated within the connection encasement 31 (see FIG. 6); and said body 11 having a different width at the frontal side and the lateral side. Moreover, the body 11 comprises a square fixed ring 14, which is a right-angled plate, situated at the lower part of said body 11; a detachment part 15 which connects the square fixed ring 14 to the part extending from the body fixed screw 16 at the lower part thereof; and a detachment knob 17 at the lower part of said body fixed screw 16.

Figure 5:
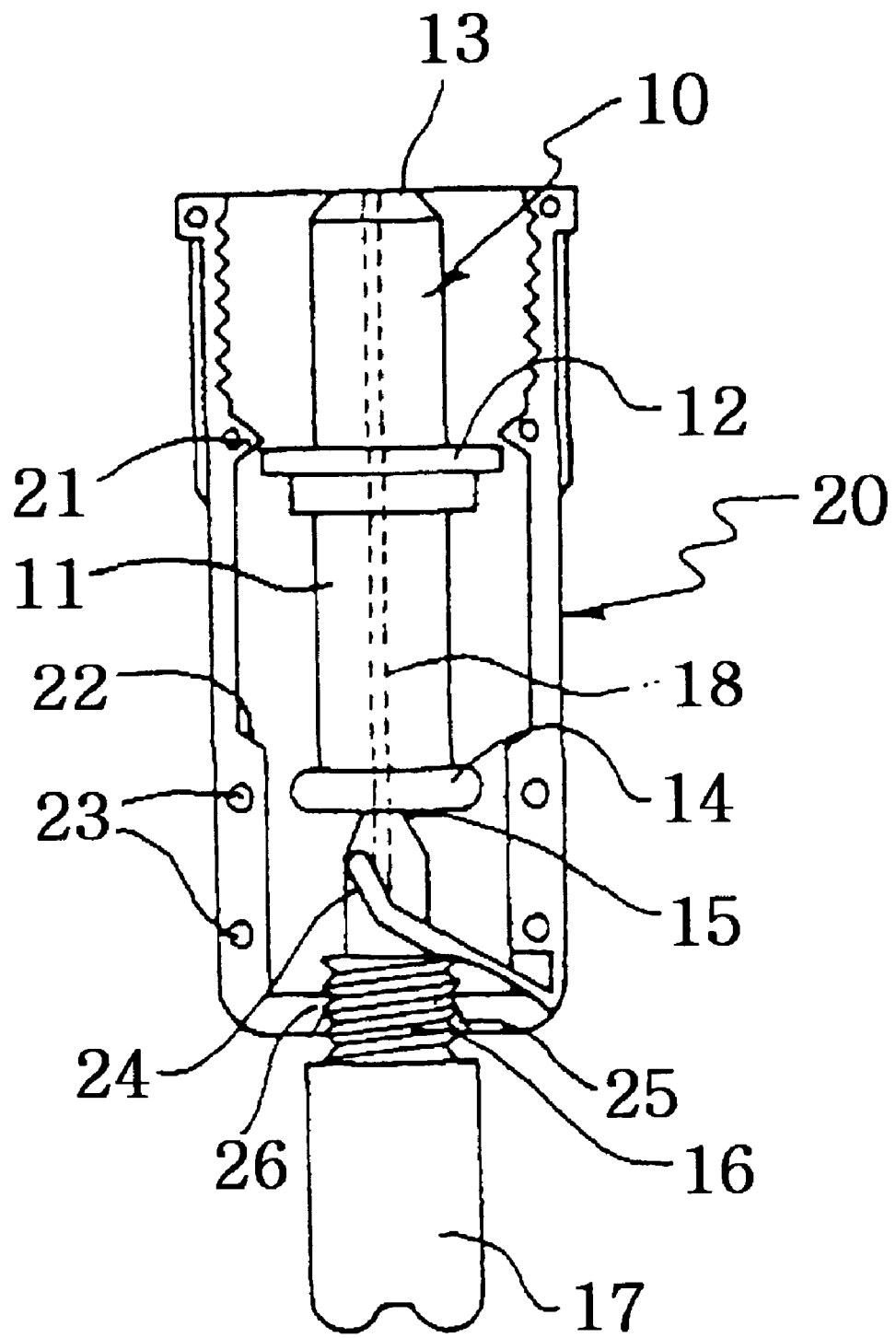
FIG. 5 is an interior structural diagram of the present invention.

The square fixed ring 14 and the detachment knob 17, respectively, have a different width at the frontal side and the lateral side. In other words, as shown in FIG. 3, the blood-collecting needle 10 comprises a body 11, a square fixed ring 14, and a detachment knob 17, all of which have a narrower width at the lateral side and a wider width at the frontal side (as shown in FIG. 5). The square fixed ring 14 therein prevents twisting of direction by turning during the separation of the detachment knob 17.

The body fixed screw 16 has a thread on the circumference thereof, as integrated therein, which is screwed onto the needle stop projection 26 of the cap 20, thereby uniting the cap 20 to the blooding-collect needle 10. The detachment part 15 is a part, which is formed between the square ring 14 and the part extending from the body fixed screw and connects the square fixed ring 14 to the part extending from the body fixed screw 16. Also, the detachment part 15 can be easily disconnected by twisting the detachment knob 17 by force towards one direction.

Figure 6:
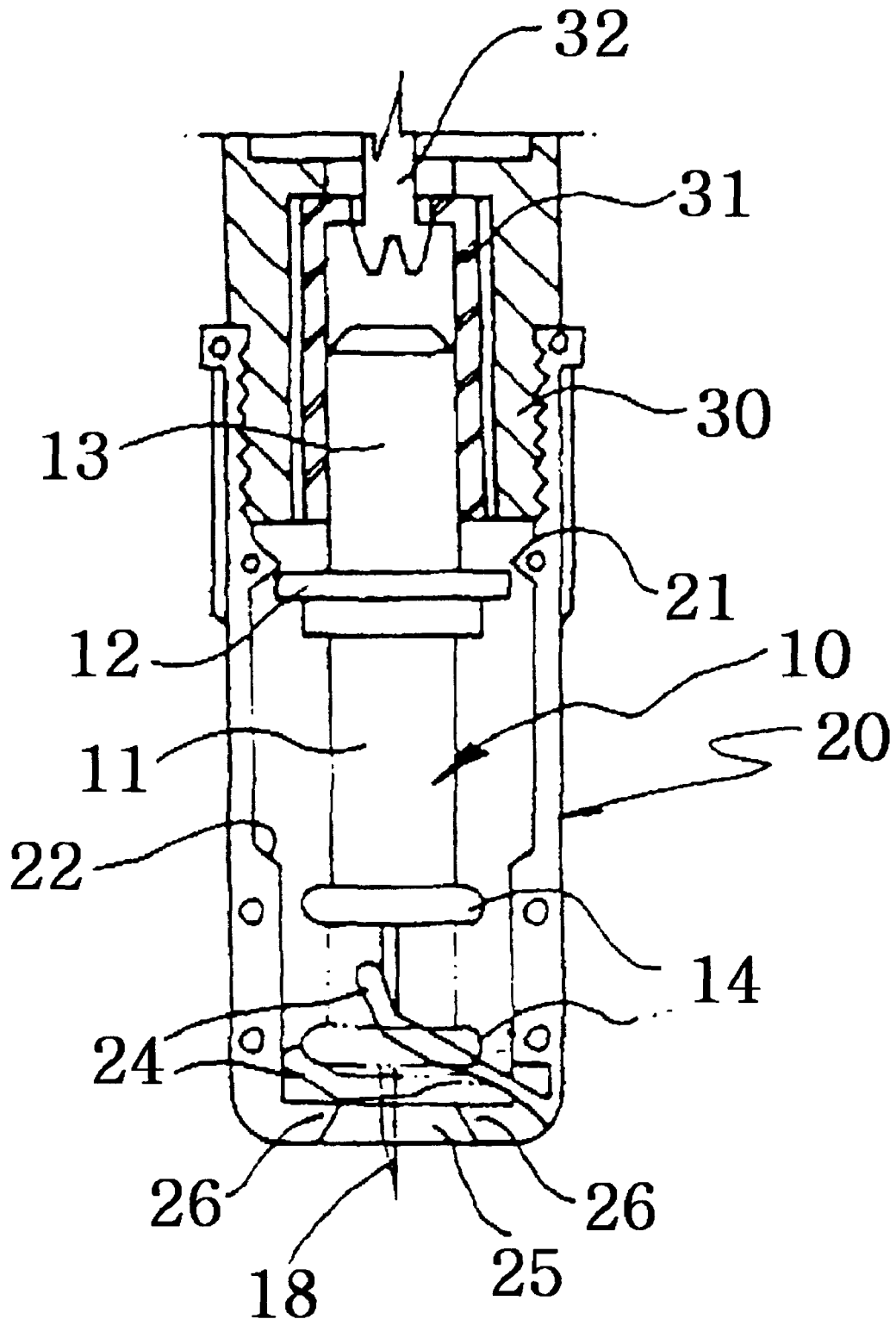
FIG. 6 is a sectional drawing, which shows the installment and use of the present invention.

As shown in FIG. 4, the cap 20 is a barrel having a larger diameter at the upper part and a lesser diameter at the lower part. More particularly, the upper part thereof is a cylindrical barrel, and the lower part thereof is a barrel having a narrower width from the lateral view. Further, as shown in FIG. 6, on the inner circumference of the upper part thereof, there is a screw thread part corresponding to the cap connecting screw 30 of a cylinder. At the lower part of the screw thread, the stop ring 12 is caught onto the stop projection 21, which prevents further intrusion to the upper part thereof. From a set distance (generally from 10–33 mm) from said stop projection 21, at the lower part thereof, there is a stroke stop projection 22. In other words, the blood-collecting needle 10 moves within the distance to the extent of said stop ring 12 as between the stop projection 21 and the stroke stop projection 22. In other words, the blood-collecting needle 10 moves within the distance to the extent of said stop ring 12 as between the stop projection 21 and the stroke stop projection 22 at an inner surface of the lower part of the cap 20. A return spring 24 is installed inside the lower part of a barrel having a narrower width from the lateral view. The starting portion of the return spring 24 is integrated into the inside surface of the cap 20, which in turn forms a needle stop projection 26. As shown in FIG. 5, the terminal part thereof is made to protrude at an angle towards the square fixed ring 14 of the blood-collecting needle 10. As shown in FIG. 6, the terminal part of the return spring 24 is positioned in such a way to be flush with the needle 18, exposed after the separation of the detachment knob 17. The return spring is positioned at one side of the needle 18 so that it does not interfere with the needle 18. The return spring 24 may be integrated into the cap 20 although it may also be made separately from the cap 20 at the aforementioned position.

Moreover, at the center of the upper part of a barrel, there is a slot 25 for withdrawing the terminal part of said needle 18 towards the target. The inlet side of the slot 25 has a larger diameter than its outlet side, and the needle stop projection 26 is formed at the lower end of the barrel adjacent to slot 25. In other words, the body fixed screw 16 of said blood-collecting needle 10, as screwed thereon, is caught onto the needle stop projection 26. During lowering of the blood-collecting needle 10, the square fixed ring 14 comes in contact with the rim of said needle stop projection 26, which in turn stops further lowering.

Moreover, the cap 20 comprises a barrel, separable into left and right sections, the respective section of which has several assembly slots 23 as shown in FIG. 5, or several insertion protrusions (not illustrated) which are fitted into said assembly slots 23. Accordingly, the cap 20 comprises a barrel of respective sections in unit by fitting said insertion protrusions into the assembly slots 23.

In the present invention, after connecting the blood-collecting needle 10 into the cap 20 as shown in FIG. 5, the cap 20 is then connected to the cap connection screw 30 of a cylinder, which is used as a gun. Then, when the body fixed screw 16 is screwed onto the needle fixed projection 26 at the slot 25, the blood-collecting needle 10 is positioned vertically in the center of the cap 20. At that time, the blood-collecting needle 10 is positioned in such a way that the upper side of the circumference of the stop ring 12 is in contact with the stop projection 21 of the cap 20.

In this state, as shown in FIG. 6, with connection to the cap connection screw 30 of the cylinder 10, the connection rod 32 of the blood-collecting needle 10 is also seated within connection encasement 31.

Consequently, while holding the detachment knob 17 by fingers, if it is slowly turned, the screw thread of the body fixed screw 16 is rotated along the inner circumference of the needle stop projection 26, gradually moving downward. Simultaneously, the detachment part 15 detaches therefrom, which had connected the square fix ring 14 to the connecting rod of the body fix screw 16. Then, if the detachment knob 26 is held and turned to the full extent, it becomes completely separated from the cap 20. At that time, at the lower part of the square fix ring 14, the point end of the needle 18 becomes exposed thereby. Since the square fix ring 14 is positioned at the lower part of the barrel of the cap 20 with narrower width, the blood-collecting needle 10 is impeded from twisting by rotation.

In this state, if the button is pressed, the blood-collecting needle 10 is instantly lowered. At the same time, the square fixed ring 14, while pushing the return spring 24, is lowered as well, and then the needle 18 is instantly withdrawn through the slot 25 for collecting blood. Then, the blood-collecting needle 10 comes in contact with the area where the base of the square fixed ring 14 is at the stroke stop projection 22, which in turn stops further lowering. In this state, there is a force that causes the return spring 24, which had been lowered simultaneously with the square fix ring 14, to return to its original position. By this force, the blood-collecting needle 10 is lifted to its original position. Consequently, the point end part of the needle 18 is once again repositioned inside the cap 20.

Consequently, after collecting blood, the blood-collecting needle 1 is set to its original position. In this state, the cap 2 is detached from the cylinder and thrown away in the depository. At that time, the blood-collecting needle 10 is inside the cap 20, positioned deep inside from the slot via a return spring 24, the fact of which ensures maintenance of safety control.

According to the present invention, the blood-collecting needle after use returns to its original position via a return spring. At the same time, the point end of the needle is repositioned deep inside from the slot of the cap. The blood-collecting needle and the point end of the needle inside the cap are disposed of together. Accordingly, the present invention has the effect of preventing infections of AIDS, hepatitis, or other pathogenic bacteria to persons collecting the blood or handling waste disposition.

What is claimed is:

1. A lancet having a blood-collecting needle with a safety feature, which comprises:
   (a) a cap that is connected to a cap connecting screw of a cylinder; and
   (b) a blood-collecting needle,
   wherein said cap comprises:
   (c) a barrel having a lower part that is narrower than an upper part thereof, assembled with two sections;
   (d) a screw thread corresponding to the cap connecting screw, the thread being located on an inner circumference of the upper part thereof;
   (e) a stop projection protruding from the lower part thereof;
   (f) a stroke stop projection located at an inner surface of the lower part, and at a set distance from stop projection;
   (g) a needle stop projection at a lower end of the barrel; and
   (h) an elastic return spring located at one side within the cap,
   wherein said blood-collecting needle comprises:
   (i) a stop ring located at an upper part of a body in which a needle is installed;
   (j) a connecting rod located at the upper part of the body, and seated within a connection encasement;
   (k) a square fixed ring located at a lower part of the body;
   (l) a body fixed screw, located at the lower part of the body and having a screw thread on an exterior side thereof, corresponding to said needle stop projection;
   (m) a detachment knob located at the lower part of the body; and
   (n) a detachment part located between a part extending from said body fixed screw and the square fixed ring.

* * * * *